United States Patent
Adkins

[11] Patent Number: 6,031,137
[45] Date of Patent: Feb. 29, 2000

[54] STABLE AROMATIC AMINE COMPOSITION, A PROCESS FOR PREPARING COLOR STABLE AROMATIC AMINES, AND THE PRODUCTION OF LIGHT COLORED AROMATIC AMINE-BASED POLYETHER POLYOLS

[75] Inventor: Rick L. Adkins, New Martinsville, W. Va.

[73] Assignee: Bayer Corporation, Pittsburgh, Pa.

[21] Appl. No.: 09/087,766

[22] Filed: May 29, 1998

[51] Int. Cl.[7] .................................................. C07C 209/00
[52] U.S. Cl. ........................... 564/438; 564/291; 564/296
[58] Field of Search .................................. 564/438, 291, 564/296

[56] References Cited

U.S. PATENT DOCUMENTS

| | | | |
|---|---|---|---|
| 3,264,268 | 8/1966 | Muller et al. | 260/77.5 |
| 3,314,995 | 4/1967 | Cross et al. | 260/570 |
| 3,446,848 | 5/1969 | Aitken et al. | 260/584 |
| 3,462,492 | 8/1969 | Kober | 260/573 |
| 3,499,009 | 3/1970 | Odinak | 260/570 |
| 4,168,989 | 9/1979 | Edelman et al. | 134/28 |
| 4,209,609 | 6/1980 | Haas | 528/421 |
| 4,391,728 | 7/1983 | Korczak et al. | 252/182 |
| 4,421,871 | 12/1983 | Korczak et al. | 521/167 |
| 4,562,290 | 12/1985 | Korchzak et al. | 564/399 |
| 4,877,879 | 10/1989 | Gansow | 544/402 |
| 4,988,461 | 1/1991 | Nichols | 252/182.18 |

FOREIGN PATENT DOCUMENTS

| | | |
|---|---|---|
| 1073664 | 6/1967 | United Kingdom . |
| 1311095 | 3/1973 | United Kingdom . |
| 1398185 | 6/1975 | United Kingdom . |

*Primary Examiner*—Samuel Barts
*Attorney, Agent, or Firm*—Joseph C. Gil; N. Denise Brown

[57] ABSTRACT

This invention relates to stable aromatic amine compositions. These compositions comprise a) an organic compound containing at least one carboxylic acid group, and b) an aromatic amine. This invention also relates to a process for stabilizing the color of aromatic amines, and to the use of these aromatic amines as initiators for the preparation of polyether polyols.

10 Claims, No Drawings

STABLE AROMATIC AMINE COMPOSITION, A PROCESS FOR PREPARING COLOR STABLE AROMATIC AMINES, AND THE PRODUCTION OF LIGHT COLORED AROMATIC AMINE-BASED POLYETHER POLYOLS

BACKGROUND OF THE INVENTION

This invention relates to a stable aromatic amine composition comprising an aromatic amine group containing compound and a small quantity of a carboxylic acid. The present invention also relates to a method for preventing the discoloration of aromatic amine group containing compounds, and to a process for the production of light colored aromatic amine based polyether polyols.

One of the problems or disadvantages associated with amine group containing compounds is the tendency of these compounds to discolor.

Discoloration of some amine group containing compounds such as, for example, ortho-toluenediamine (o-TDA), darken quickly upon exposure to air, while others such as, for example, aniline, are more stable and darken slower over time. The aliphatic amine group containing compounds also discolor over time at room temperature, but generally speaking, these discolor at a much slower rate than the aromatic amine group containing compounds.

U.S. Pat. No. 3,595,918 relates to the stabilization of tolylene diamine. This reference discloses that tolyenediamine can be stablized against discoloration by the addition of an ascorbic acid in an amount of 0.05% to about 5% by weight. Ascorbic acid, isoascorbic acid and their mixtures are the only compounds disclosed as being suitable for stabilizing tolyene diamine. These two compounds are actually cyclic lactones, not free carboxylic acids.

Amine group containing compounds are known to be suitable initiators for preparing polyether polyols. Various amine initiated polyether polyols and the process for their production are described in, for example, U.S. Pat. Nos. 3,264,268, 3,314,995, 3,446,848, 3,462,492, 3,499,009, 4,209,609, 4,391,728, 4,421,871 and 4,562,290, and as described in British Patents 1,073,664, 1,311,095 and 1,398,185.

U.S. Pat. No. 4,877,879 describes the stabilization of polyether polyols prepared from amine initiators in the presence of alkaline catalysts. This reference suggests that the addition of an excess amount of a reducing agent, particularly formic acid, is effective in neutralizing the alkaline catalyst, thereby stabilizing the reactivity of the polyether polyol. This is described as being particularly effective for aliphatic amine initiators containing a tertiary nitrogen as the resultant polyether reacts with an alkylene oxide to yield a dark, color-forming quaternary amine complex.

The use of discolored amine group containing compounds as initiators in the production of polyether polyols results in the polyether polyols also being discolored. The dark color of the resultant polyether polyols is irreversible. Therefore, a means of preventing discoloration of amine group containing compounds and/or reducing the color of polyether polyols started from amine group containing compounds are commercially desirable.

One way of avoiding/preventing discoloration of these amine group containing compounds and polyether polyols prepared from these compounds, is to immediately form polyether polyols from the amine group containing compounds after distillation, before they come into contact with air. This, however, requires that the amine group containing compounds and the resultant polyether polyols be produced in the same plant, with no time lapse between the point of distilling the amine containing compounds and when these are used as initiators to form polyether polyols. Otherwise, stringent engineering measures are required to ensure that the amine compounds are oxygen-free at all points in the process between the time they are purified and used. Currently, it is necessary to keep the entire process totally under nitrogen to prevent and/or minimize this discoloration.

In accordance with the present invention, it was found that the addition of a relatively small quantity of certain groups of compounds to aromatic amine compounds surprisingly formed compositions which are stable against discoloration. This is true even after storing the treated aromatic amine compositions in a 100° C. oven for 1 week. Polyether polyols can then be produced from these treated aromatic amine compounds, without the derogatory color effects one would normally expect.

SUMMARY OF THE INVENTION

This invention relates to stable aromatic amine compositions comprising:

a) from 0.001 to 10% (preferably 0.1 to 1%, most preferably from 0.1 to 0.5%) by weight, based on 100% by weight of component b), of at least one organic compound containing at least one carboxylic acid group, wherein the organic compound contains from 1 to 20 carbon atoms, preferably from 1 to 10 carbon atoms, and most preferably from 1 to 6 carbon atoms, and b) at least one aromatic amine group containing compound.

The present invention also relates to a process for stabilizing the color of an aromatic amine group containing compound. This process comprises 1) adding a) from 0.001 to 10% (preferably 0.1 to 1%, most preferably from 0.1 to 0.5%) by weight, based on 100% by weight of component b), of at least one organic compound containing at least one carboxylic acid group, wherein the organic compound contains from 1 to 20 carbon atoms, preferably from 1 to 10 carbon atoms, and most preferably from 1 to 6 carbon atoms, to b) at least one aromatic amine group containing compound. Ortho-toluenediamine is a preferred aromatic amine in which discoloration can be prevented or minimized by adding a small quantity of one of these organic compounds.

The present invention also relates to a process for the production of stable, light colored aromatic amine-based polyether polyols comprising alkoxylating an aromatic amine group containing compound, wherein b) said aromatic amine group containing compound has been treated with a) from 0.001 to 10% (preferably from 0.1 to 1%, most preferably 0.1 to 0.5%) by weight, based on 100% by weight of the aromatic amine group containing compound, of at least one organic compound containing at least one carboxylic acid group, wherein said compound contains from 1 to 20 carbon atoms, preferably from 1 to 10 carbon atoms, and most preferably from 1 to 6 carbon atoms. The addition of a small quantity of an organic compound containing at least one carboxylic acid group, wherein the compound contains from 1 to 20 carbon atoms is effective in preventing or minimizing the discoloration of aromatic amine group containing compounds, and thereby allows light colored polyether polyols to be produced therefrom.

DETAILED DESCRIPTION OF THE INVENTION

As used in the present invention, the term stable with respect to the aromatic amine compositions of the present invention means that the color of these is lighter than the standard when stored for at least 1 week at a temperature of ≧25° C. The standard is the corresponding untreated aromatic amine. The treated amine compositions varied in color from a pale pink to a ruby red, based on a visual assessment. These colors were then defined by the reflectance values (L, a, b) using a Hunterlab Color Questll unit.

In accordance with the present invention, suitable organic compounds containing at least one carboxylic acid group wherein the organic compound contains from 1 to 20 carbon atoms (preferably from 1 to 10 carbon atoms, most preferably from 1 to 6 carbon atoms) are suitable for preventing discoloration of aromatic amine group containing compounds. The number of carbon atoms set forth above is intended to be inclusive of the carbon atom in the carboxylic acid group(s). Suitable examples of these organic aliphatic compounds include, for example, mono- and polycarboxylic acid groups, aliphatic compounds containing mono- and polycarboxylic acid groups and at least one hydroxyl groups, aromatic compounds containing mono- and polycarboxylic acid groups, aromatic compounds containing mono- and polycarboxylic acid groups and at least one hydroxyl group, and compounds containing mono- and polycarboxylic acid groups and one or more ether groups, amine groups or thio groups.

The suitable aliphatic compounds containing mono- and poly-carboxylic acid groups typically contain from 1 to 20 carbon atoms, inclusive of the carbon atoms present in the carboxylic acid group(s). It is preferred that aliphatic compounds containing mono- and polycarboxylic acid groups contain from 1 to 20 carbon atoms and from 1 to 6 carboxylic acid groups. Suitable aliphatic groups may be branched or linear. Some examples of these aliphatic compounds include formic acid, acetic acid, propionic acid, acrylic acid, butyric acid, valeric acid, oxalic acid, etc. Preferred compounds are formic acid and acetic acid.

Suitable aliphatic compounds containing mono- and polycarboxylic acid groups which additionally contain one or more hydroxyl groups typically contain from 2 to 20 carbon atoms, inclusive of the carbon atoms present in the carboxylic acid group(s). It is preferred that aliphatic compounds containing mono- and polycarboxylic acid groups and one or more hydroxyl groups, contain from 2 to 20 carbon atoms, and from 1 to 6 carboxylic acid groups, and from 1 to 8 hydroxyl groups. Suitable aliphatic compounds may be branched or linear. Some examples of these compounds include glycolic acid, citric acid, lactic acid, 12-hydroxy stearic acid, gluconic acid, mucic acid, etc. A preferred compound is glycolic acid.

Suitable aromatic compounds containing mono- and polycarboxylic acid groups typically contain from 7 to 20 carbon atoms, inclusive of the carbon atoms present in the carboxylic acid group(s). It is preferred that aromatic compounds containing mono- and polycarboxylic acid groups contain from 7 to 20 carbon atoms, and from 1 to 6 carboxylic acid groups. It is not necessary for the carboxylic acid group(s) of these compounds to be attached directly to an aromatic ring. Some examples of these aromatic compounds include benzoic acid, phthalic acid, 1,2,4,5-benzene-tetra-carboxylic acid, phenylacetic acid, phenylmalonic acid, etc. A preferred compound is benzoic acid.

The suitable aromatic compounds containing mono- and poly-carboxylic acid groups which additionally contain one or more hydroxyl groups typically contain from 7 to 20 carbon atoms, inclusive of the carbon atoms present in the carboxylic acid group(s). It is preferred that aromatic compounds containing mono- and polycarboxylic acid groups and one or more hydroxyl groups, contain from 7 to 20 carbon atoms, and from 1 to 6 carboxylic acid groups, and from 1 to 5 hydroxyl groups. Some examples of these aromatic compounds include salicylic acid, 4-hydroxyphenylacetic acid, mendelic acid, dihydroxyphenylacetic acid, dihydroxymandelic acid, etc. Salicylic acid is a preferred compound.

Suitable aliphatic and aromatic compounds which contain mono- and polycarboxylic acid groups and one or more ether groups, amine groups and/or thio groups typically contain from 2 to 20 carbon atoms, inclusive of the carbon atoms present in the carboxylic acid group(s). It is preferred that compounds containing mono- and polycarboxylic acid groups contain from 2 to 20 carbon atoms and from 1 to 6 carboxylic acid groups. Some examples of these compounds include mercaptoacetic acid, β-mercaptopropionic acid, thiosalicyclic acid, methoxyacetic acid, phenoxyacetic acid, 2-aminoacetic acid, 2-aminobenzoic acid, pyrrole-2-carboxylic acid, etc. Preferred compounds of this group include methoxyacetic acid and thiosalicylic acid.

Carboxylic acids suitable for the present invention may be prepared by any of the known processes in the art. Examples of suitable processes are described in, for example, *Kirk Othmer Encyclopedia of Chemical Technology*, Fourth Edition, Vol. 5, pp. 168–178, and Vol, 11, pp. 951–958. Formic acid, for example, may be prepared by the carbonylation of methanol using carbon monoxide.

In general, suitable aromatic amine group containing compounds of the present invention have molecular weights of less than about 500, preferably less than about 400, and more preferably less than 200. Suitable aromatic amine group containing compounds include, for example, those compounds wherein at least 1 amine group is, and preferably 1 to 3 amine groups are, attached to an aromatic ring, and the aromatic ring may be substituted or unsubstituted. Suitable substituents for the aromatic ring include, for example, alkyl groups having from 1 to 18 carbon atoms which may be branched or linear such as, for example, methyl, ethyl, propyl, etc.; aromatic groups having from 6 to 13 carbon atoms such as, for example, phenyl, aminophenyl, and diaminophenyl; and arylalkyl groups having from 7 to 12 carbon atoms such as, for example, methylene(aminophenyl), 2-(aminophenyl)butyl, etc. Suitable substituents for the aromatic ring also include hydroxyl groups. Aminophenol is one example of a compound wherein the aromatic ring is substituted with an hydroxyl group. Also, suitable as the aromatic amine group containing compound of the present invention are fused ring systems containing from 10 to 20 carbon atoms. Diaminonaphthalene is one example of a suitable fused ring system for the present invention.

Examples of suitable aromatic amines for the present invention include compounds such as aniline, diaminobenzene, triaminobenzene, tetraaminobenzene, tetraaminobiphenyl, methylene dianiline, crude toluenediamine (i.e., a mixture of the various isomers), and ortho-toluenediamine (i.e., an isomeric mixture of primarily 2,3-TDA and 3,4-TDA in a weight ratio of about 60 to about 40). Ortho-toluenediamine and crude toluenediamine are preferred aromatic amines in the present invention.

The preparation of suitable amines for the present invention is well known to those skilled in the art. For instance, suitable amines can be prepared by dinitrating toluene with nitric acid in the presence of sulfuric acid or other catalyst to yield isomers of dinitrotoluene, which are then reduced with hydrogen to yield crude toluenediamine. (See, for example, *Kirk-Othmer Encyclopedia of Chemical Technology*, Fourth Edition, "Amines by Reduction", Volume 2, pp. 483–501, and "Nitrobenzene and Nitrotoluenes", Volume 17, pp. 133–151.) Crude TDA is a mixture of the various isomers, i.e., 2,3-TDA, 2,4-TDA, 3,4-TDA, 2,5-TDA, and 2,6-TDA.

In the process of the present invention, discoloration of aromatic amines is prevented or minimized by adding a small quantity of at least one carboxylic acid containing from 1 to 20 carbon atoms to aromatic amines as soon as possible after the formation and subsequent purification of these amines. The time after an amine is prepared and the point in time at which the addition of a small quantity of a carboxylic acids is necessary to be effective in preventing discoloration of the amine ultimately depends on the stability of the particular amine with respect to discoloration and how well it is protected from contact with air.

Some relatively stable amines such as, for example, aniline, darken slowly over time while other amines are relatively unstable and darken immediately upon exposure to air. Ortho-toluenediamine is one example of a relatively unstable amine which darkens immediately when exposed to air. Accordingly, the point at which the stabilizing compound (i.e., carboxylic acid) is added to the amine to prevent discoloration may vary. It is, however, preferred that a small quantity of a carboxylic acid is added to the amine immediately following distillation. The stabilizing compounds may be added at a later point, if the freshly prepared amine is kept oxygen-free under an inert gas, such as, for example, nitrogen or argon. Once the stabilizing compound(s) has been added to the aromatic amine compound, the resultant composition is relatively stable in terms of color changes.

Typically, in a conventional process, when the nitrogen system fails or a leak occurs in the system protecting the amine group containing compound from exposure to air, the amine group containing compound begins to darken. Ortho-toluenediamine and crude TDA, the preferred amine group containing compounds, start to darken immediately upon exposure to air. The presence of a stabilizing agent such as, for example, formic acid, helps protect the color of the amine compound until the nitrogen can be restored.

It is, of course, possible to form polyether polyols wherein the previously described aromatic amines treated with a small quantity of at least one carboxylic acid containing from 1 to 20 carbon atoms are the initiators instead of conventional untreated aromatic amines. A polyether polyol prepared from the color stable aromatic amine has a lighter color than a polyether polyol prepared from an untreated aromatic amine. Polyether polyols based on these treated aromatic amine initiators in accordance with the present invention can be prepared by any of the known processes such as are described in, for example, U.S. Pat. Nos. 4,209,609 and 4,421,871, the disclosures of which are herein incorporated by reference, and as described in British Patent 1,398,185. In general, the amine-initiated polyether polyols of the present invention are prepared by reacting an alkylene oxide with an amine having an amine functionality of at least 1, optionally in the presence of an alkaline catalyst. Typically, up to 2 epoxide molecules can be added to a primary amine group without the use of a catalyst. If, however, more than 2 epoxide groups per amine are desired, an alkaline catalyst is generally used to promote the reaction.

The suitable amine initiators for preparing polyether polyols include those previously described which have been treated with a carboxylic acid as described above. Some examples of alkylene oxides useful in producing the polyether polyols of the present invention include: ethylene oxide, propylene oxide, butylene oxide, and mixtures of these alkylene oxides. Combinations of ethylene oxide and propylene oxide are particularly preferred. In principle, any alkaline material capable of catalyzing the epoxidation reaction of the present invention may be used. Specific alkaline catalysts which have been found to be particularly suitable include, for example, potassium hydroxide and sodium hydroxide.

In general, the epoxidation reaction occurs by contacting the amine having an amine functionality of at least 1 with the alkylene oxide(s) at an elevated temperature in the range of from 90 to 180° C. under moderately elevated pressure, optionally in the presence of the alkaline catalyst. The amounts of amine and alkylene oxide which are used are generally 1 to 10 equivalents of alkylene oxide for each equivalent of amine. The epoxidation product generally has an average hydroxyl value (determined by ASTM D-2849-69 hydroxyl number method C) of at least 28, preferably in the range of from about 250 to about 1200. The molecular weights of the polyether polyols of the present invention (number average determined by end group analysis and nominal functionality of the polyol) preferably range from about 150 to about 1500, more preferably from about 300 to about 1200, and most preferably from about 400 to about 1000.

After the polyol has been prepared, the resultant reaction mixture which contains the alkaline catalyst in amounts of from about 0.1% to about 1.0% as KOH is neutralized with an acid such as, for example, sulfuric acid, phosphoric acid, lactic acid or oxalic acid. Neutralization may be accomplished by mixing the acid and reaction mixture at ambient conditions with stirring, then distilling to remove any excess water. The neutralized polyether polyol need not have a pH of exactly 7.0. The reaction mixture may be maintained at a slight acidity or alkalinity, i.e., at a pH of from 5 to 11, preferably from 6 to 10. If the salt formed is soluble in the polyol, it may be left in. Otherwise, the salt can be removed by, for example, filtration.

The neutralized polyether polyol reaction mixture of the present invention is clear, i.e., free from haze and may be used directly in processes for the production of polyurethane foams. Methods for the production of polyurethane foams by reacting these polyether polyols with polyisocyanates via the polyisocyanate addition process are well known to those in the art.

The following examples further illustrate details for the preparation and use of the compositions and processes of this invention. The invention, which is set forth in the foregoing disclosure, is not to be limited either in spirit or scope by these examples. Those skilled in the art will readily understand that known variations of the conditions and processes of the following preparative procedures can be used to prepare these compositions. Unless otherwise noted, all temperatures are degrees Celsius and all parts and percentages are parts by weight and percentages by weight, respectively.

EXAMPLES

In the working examples of the present invention, the colors of treated aromatic amine compounds were determined by a visual comparison with a pink-red color scale. Reflectance values of this scale were determined using a Hunterlab Color QuestII unit. In the untreated samples of aromatic amine compounds, the color of the sample was too dark to accurately measure reflectance values, so the color of these samples is reported as the Gardner color. The reflectance values are reported in terms of L, a and b values for each sample.

Example 1

100 g. of freshly distilled ortho-toluenediamine (o-TDA) were placed in a bottle. To this, 0.6 g. of acetic acid was added, followed by mixing thoroughly. The sample was sealed, and placed in a 100° C. oven, along with a sealed sample of 100 g. of untreated, freshly distilled ortho-toluenediamine (see Example 5 in Table 1). After 24 hours, the untreated sample had a Gardner color >18, but the treated sample had a color such that the reflectance values were L=49.31, a=46.90 and b=18.43. After 48 hours, the untreated sample of o-TDA was opaque black (i.e., the Gardner color was >18, whereas the sample treated with acetic acid still had a color such that the reflectance values were L=49.31, a=46.90 and b=18.43. After 1 week, the color of the o-TDA sample treated with acetic acid remained such that the reflectance values were L=49.31, a=46.90 and b=18.43.

Examples 2–4

These examples were performed using an essentially identical procedure as set forth under Example 1, with the exception of the particular stabilizing compound which was added to the freshly distilled o-TDA and the amount of each stabilizing compound. Specific stabilizing compounds and the relative quantity of each, as well as the result on the reflectance values of the color, or where appropiate, Gardner color, after storage in a 100° C. oven for 24 hours, 48 hours, and for 1 week are shown.

TABLE 1

EFFECT OF TREATMENT OF O-TDA WITH ADDITIVES ON COLOR

| Example | Additive | Weight (grams) | Reflectance Values[1] |
|---|---|---|---|
| 1 | Acetic acid | 0.6 | L = 49.31; a = 46.90; b = 8.43 |
| 2 | Benzoic acid | 1.2 | L = 49.31; a = 46.90; b = 8.43 |
| 3 | Formic acid | 0.5 | L = 88.08; a = 4.26; b = 6.91 |
| 4 | Propionic acid | 0.7 | L = 49.31; a = 46.90; b = 8.43 |
| 5 | Untreated | — | >18 (opaque black)[2] |

[1]represents Hunterlab Color QuestII reflectance values after storage for 24 hours in a 100° C. oven. These reflectanoe values were unchanged after storage in a 100° C. oven for 48 hours and after 1 week.
[2]represents Gardner color after storage for 24 hours in a 100° C. oven.

Examples 6–7

100 g. of freshly distilled aniline were placed in a bottle. To this was added 0.5 g. of formic acid, followed by mixing thoroughly. The sample (Example 6) was sealed and placed in a 100° C. oven , along with a sealed sample of 100 g. of untreated, freshly distilled aniline (Example 7). After 7 days, the untreated sample had a Gardner color=16 (Example 7), but the treated sample had a Gardner color=3.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for stabilizing the color of an aromatic amine group containing compound, comprising:

1) adding from 0.001 to 10% by weight, based on 100% by weight of b), of a) at least one organic compound containing at least one carboxylic acid group, wherein said organic compound containing from 1 to 20 carbon atoms, to b) an aromatic amine group containing compound.

2. The process of claim 1, wherein a) said organic compound containing at least one carboxylic acid group is an aliphatic compound having from 1 to 6 carboxylic acid groups.

3. The process of claim 2, wherein a) said organic compound additionally contains from 1 to 6 hydroxyl groups.

4. The process of claim 1, wherein a) said organic compound containing at least one carboxylic acid group is an aromatic compound containing from 7 to 20 carbon atoms and having from 1 to 6 carboxylic acid groups.

5. The process of claim 4, wherein a) said organic compound additionally contains from 1 to 5 hydroxyl groups.

6. The process of claim 1, wherein a) said organic compound containing at least one carboxylic acid group is an aliphatic compound containing from 2 to 20 carbon atoms, having from 1 to 6 carboxylic acid groups, and additionally containing one or more ether groups, one or more amine groups and/or one or more thio groups.

7. The process of claim 1, wherein a) said organic compound containing at least one carboxylic acid group is an aromatic compound containing from 7 to 20 carbon atoms, having from 1 to 6 carboxylic acid groups, and additionally containing one or more ether groups, one or more amine groups and/or one or more thio groups.

8. The process of claim 1, wherein a) said organic compound containing at least one carboxylic acid group is an organic compound additionally containing one or more amine groups.

9. A process for the production of a polyether polyol comprising alkoxylating an aromatic amine, wherein said aromatic amine is treated with from 0.001 to 5% by weight, based on 100% by weight of at least one organic compound containing at least one carboxylic acid group, wherein said organic compound contains from 1 to 20 carbon atoms.

10. A stable aromatic amine composition comprising:

a) from 0.001 to 10% by weight, based on 100% by weight of component b), of an organic compound selected from the group consisting of acetic acid, formic acid, benzoic acid, propionic acid and mixtures thereof; and b) an aromatic amine group containing compound having a molecular weight of less than about 500.

* * * * *